United States Patent
Ace

(10) Patent No.: US 6,342,211 B1
(45) Date of Patent: Jan. 29, 2002

(54) DIFFERENTIAL LUBRICANTS

(76) Inventor: Ronald S. Ace, 15706 Bond Mill Rd., Laurel, MD (US) 20707

( * ) Notice: Subject to any disclaimer, the term of this patent is extended or adjusted under 35 U.S.C. 154(b) by 0 days.

(21) Appl. No.: 09/575,983

(22) Filed: May 23, 2000

Related U.S. Application Data

(60) Provisional application No. 60/138,293, filed on Jun. 9, 1999.

(51) Int. Cl.[7] .................................................. A61K 7/15
(52) U.S. Cl. ......................................... 424/73; 424/401
(58) Field of Search .............................. 424/401, 70.1, 424/70.11, 70.17, 73

(56) References Cited

U.S. PATENT DOCUMENTS 3,072,536 A * 1/1963 Pye .............................. 167/85
6,106,809 A * 8/2000 Bhatt et al. .................... 424/45

FOREIGN PATENT DOCUMENTS

GB        2 236 760 A   *   4/1991

* cited by examiner

*Primary Examiner*—Jose'G. Dees
*Assistant Examiner*—K M George
(74) *Attorney, Agent, or Firm*—Jones, Tullar & Cooper, PC

(57) ABSTRACT

A di-lubricant for shaving comprises a low concentration of polyacrylamides suspended in water to provide lubrication for skin but not for hair.

1 Claim, 1 Drawing Sheet

DIFFERENTIAL LUBRICANTS

This application claims the benefit of Provisional Application No. 60/138,293, filed Jun. 9, 1999.

BACKGROUND OF THE INVENTION

The present invention relates, in general, to lubricants for use in shaving, and more particularly to a new class of hair shaving lubricants, herein called "differential lubricants" (or "di-lubricants") which only highly lubricate skin, but not hair shafts.

Prior art lubricated hair shaving is based on the assumption that skin, hair, and razors should be highly lubricated, and an entire shaving lubricant industry has been built around the reduction of skin damage and longevity between shaves. The main purpose of the entire global shaving lubricant industry is to achieve the closest shave without pain or discomfort. However, the underlying physics principles of shaving hair has, until now, remained flawed.

Lubricated hair shaving is believed to predate recorded history. To everyone who has attempted or experienced razor shaving without a lubricant, it becomes obvious that severe skin damage always occurs. Even with lubrication, nicks, cuts, razor burn, rough skin, chemical irritation, and the like, are common, and skin lubrication is absolutely necessary for very close razor shaving. It is no surprise, then, that the shaving lubricant industry is a multibillion dollar industry. Ever since the original discovery of lubricated shaving, the need for increasing general lubrication of skin, hair, and razor has been promoted.

The technological art of lubricated hair shaving has been improved, with the introduction of sharper razor blades and better lubricants, to such degrees that one no longer thinks of shaving hair at the skin level, but below the skin level. Microscopic hair length differences smaller than 0.001 inch can easily be discerned. Therefore, to further improve the art of mechanical shaving, microscopic laws of physics about hair, skin and, razors must be elaborated. Lubricated shaving centers on three objectives—closeness and longevity of each shave, minimizing skin damage, and minimizing chemical toxicity.

Lubricated shaving continues to be favored over electric dry razor shaving for several reasons. Wet razor shaving permits far higher applied skin pressure (force per unit area) and thus, it forces hair shafts farther upward from the dermal tissues just before being cut. The inherent advantages derived from the much higher skin pressures of wet shaving also demand high lubrication to prevent skin damage. Therefor, prior art shaving lubricants seek to achieve the highest skin lubricating properties in order to permit application of the greatest skin pressure and hence, the closest shaves. That approach is reasonable, until a closer microscopic examination of the physics of cutting hair is conducted. Prior art lubricants seek to provide maximum skin lubrication without regard to the fact that microscopic hair lubrication occurs at the same time. However, if hair shafts and razor cutting edges are highly lubricated like skin, undesirable microscopic slippage takes place just before the microscopic cut begins on each hair shaft. That same lubricated microscopic slippage continues as the razor slices through each hair shaft. Such lubricated slippage on hair shafts effectively lengthens the cut hair by several thousandths of an inch, which is equivalent to almost one days' growth. As minute as a few thousandths of an inch might seem, in reality, it represents a large percentage of daily hair growth, as well as a large measure of the over all quality of shaving. Hair grows at varying rates, approximating 1–3 hair-diameters per day. Typical male facial hair is about 0.005–0.008 inch in diameter, and grows about 0.005 to 0.010 inch in length per day. Female leg hair is typically finer and grows more slowly. If hair protrudes just 0.001 to 0.002 inches above skin level, it can easily be detected by human touch. By the time hair has grown 0.003 to 0.004 inches above skin level, hair stubble is quite visible and a shave is warranted. Hence, the closer the shave and the farther below the skin level a shave can be achieved, the longer the shave will last before the hair is detected again.

For example, assume that a single 0.007 inch diameter hair shaft is theoretically cut off perfectly perpendicular to the shaft, and 0.004 inches below the skin surface. One day later, at a 0.008 inch/day growth rate, that hair will have grown 0.008 inches and will again protrude 0.004 inches above the skin level. Next, visualize a highly lubricated 0.007 inch diameter hair being shaved. Instead of the hair being ideally cut straight across from the initial razor contact point, instead, the lubricated razor will microscopically slide up the lubricated hair shaft before it begins cutting through the hair. Then, prior art lubricants continue to lubricate the actual cutting action as the razor slides through the hair shaft, producing an upward motion and a sloped, or tapered, hair end. The final result of lubricating hair is a tapered cut, typically at less than 60 degrees instead of the ideal 90 degree perpendicular hair shaft cut. A typical 0.007 inch diameter hair shaft cut at just 45 degrees will be sharp and pointed and about 0.003 to 0.004 inches longer than one perpendicularly cut at the ideal 90 degrees (see FIG. 1). In other words, a lubricated hair can not be as bluntly cut because lubricants allow slippage in two ways—slippage on the initial contact before cutting and also slippage during cutting. The resulting sharp pointed hair ends protrude upwardly an amount equal, in many cases, to more than a half day's growth as compared to an ideal blunt cut hair shaft which may be several thousandths of an inch shorter. Clearly, therefore, hair shafts should be microscopically totally unlubricated for the closest shave. And yet, skin must be lubricated for the absolute minimum friction. These two diametrically opposed requirements (high skin lubrication and zero hair lubrication) seem to be impossible to obtain from a single lubricant or even from a combination of lubricants. Nevertheless, as will be shown, the present invention does indeed simultaneously exhibit both of these diametrically opposing properties.

Prior art shaving lubricants not only make the error of lubricating skin and hair, but they also are much more toxic than most people perceive. The term "Generally regarded as safe" (or "GRAS") does not mean "Non toxic". The popular presumption that "GRAS" means "safe if not ingested" is incorrect. As used in the present disclosure, "Toxic" is defined as any amount of any substance entering the body, through any means, which stresses bodily organs or functions or which do not nutritionally support normal healthy bodily processes. This broadened definition of toxicity does not embrace GRAS principles, which are directed more towards "toxic limits of endurance".

Sadly, there are almost no government regulations on cosmetic shaving lubricants, yet many toxic chemicals are present in virtually every commercial shaving lubricant. The popular belief is that if these toxic shaving substances are not ingested, they are safe, but that belief is unwarranted. Exhaustive research conducted by a pharmaceutical company, Innovative Dermal Applications, GmbH in Germany, has only recently revealed some of the limitations and physics of how skin protects against microorganisms and toxic chemicals. For example, it is now known that skin is an excellent biological barrier because skin's outermost horny layer (the stratum corneum) composes only 10% of the skin's thickness, but contributes about 80% to the permeability barrier. The horny layer is a microporous barrier, which only allows passage of less than 1 nanometer diameter molecules. That is, 1 nanometer molecules will freely pass through healthy dry skin. Most molecules of less than a few thousand molecular weight (MW), such as pharmaceutical drugs and most toxins, are much smaller than 1 nanometer in physical size. Therefore, they readily pass directly through skin directly into the capillary blood stream or via the lymphatic system into the blood stream. However, when skin is exposed to hot water and becomes fully hydrated, the crevasses in the micro-porous horny layer widen to as much as 20–100 nanometers. Usually, shaving involves hot water skin hydration and under these conditions is much more porous and can transport even extremely large molecular toxins (compounds in excess of 1,000,000 MW) directly into the body. Unfortunately, generally available commercial shaving lubricants contain significant quantities of known toxins of relatively low molecular weight which not only can, but do enter the human body during every shave. Toxic dosage is directly proportional to the exposed skin area (and the type of skin as well). Large areas, like female legs for example, are regularly and frequently exposed to 15 to 20 times that of men's faces. Most women are therefore exposed to much higher toxic loading than men.

Colorant dyes, fragrances, petroleum oils, synthetic oils, and numerous chemical additives are present in most shaving lubricants, and frequent exposures can be very deleterious to human health. The most popular pressurized commercial shaving foams and gels contain innumerable low and medium molecular weight toxins such as highly flammable pentane, with a toxic exposure limit of only 600 PPM, triethanolamine (damages liver and kidneys), menthol (an irreversible irritant/allergen), colorant dyes, synthetic lubricants, fragrances, and countless other similar toxic chemicals, all of which pass through skin to challenge vital organs. These chemicals and gases are usually used in small closed rooms where they are absorbed through wet skin, and are breathed and rebreathed. Aside from all these chemical threats, the pressurized containers themselves may also rocket and explode under heat or fire. Most of these warnings are published and publicly available in the commercial shaving lubricant's product Material Safety Data Sheets (MSDS). What is not clearly spelled out is how easily they enter the body through the skin each time they are used.

Several prior art shaving lubricant patents (not di-lubricants) serve to reinforce this point. One patent teaches the use of moderate concentrations (0.5% to 4% by weight) of water soluble, lubricating polymers such as polyacrylamide, but it only observes the obvious and well known high lubricity characteristics of polyacrylamide, like all prior art shaving lubricant inventions; it totally disregarded potentially lethal toxicity and was oblivious to the existence or the importance of di-lubricity. Another patent proposed the blending of soaps and detergents plus small quantities of polyacrylamide to form hand lathering lubricants did not mention that mixing hydrated polyacrylamide with other soap and detergent lubricants of much lower lubricating properties causes the composite mixture to largely assume the lower lubricating properties of the smaller molecular weight soaps and detergents. The much higher lubricating properties of hydrated polyacrylamide are mostly lost in the proposed hand lathering mixture. What is needed is maximum skin lubricity. Most importantly, the high concentrations of the soaps and detergents (all of quite low molecular weight) all cause skin, and especially hair, to be highly lubricated, when it will be shown in the present invention, that hair should not be lubricated at all. Furthermore, the patent proposes adding polyacrylamide as small as 500,000 molecular weight, without recognizing that such low molecular weight acrylamide polymers (500,000) cannot be made without also introducing dangerously high concentrations of unpolymerized highly toxic acrylamide monomers (several percent), as well as smaller polymer chains (such as 50,000 MW) polymer chains. Both the toxic unpolymerized acrylamide monomers as well as the smaller chains of polyacrylamide can, upon application to the skin, migrate through the skin into the body. Skin porosity characteristics and toxicity was of no importance in that invention. In a similar fashion, another polyacrylamide-containing patent proposed adding small amounts of polyacrylamide to a wide variety of high concentrations of other lubricants to produce aerosol foaming shaving lubricants. As previously pointed out, the addition of lubricants of lower lubricity to one of higher lubricity significantly reduces the over-all lubricity of the highest lubricant. In addition, the patent also aims exclusively at general lubrication of skin and hair without recognizing the fundamental importance of not lubricating hair.

There is a large and rapidly growing body of scientific evidence that strongly supports the thesis that every exposure to small doses of known toxins, which are present in literally hundreds of consumer products, produces, at the very least, a compromised immune system and stressed vital organs. Although most shaving lubricant manufacturers publish their products as GRAS products, when the toxicity of those products is combined with the nearly endless list of other toxic products (particularly cosmetics) to which people are regularly exposed, the GRAS principle is greatly diminished. Diminished health is a subtle but real result of these multiple toxic exposures. Shaving lubricants should be especially nontoxic because they are so regularly used and because they cover such high skin surface areas, under the most vulnerable hydrated conditions. Unfortunately, in order to obtain the desired lubricating properties, manufacturers have only been able to achieve moderate toxicity. As will be shown, the present invention achieves this important, essentially zero toxicity objective, without compromising the new property called di-lubricity.

SUMMARY OF THE INVENTION

Therefore, the objectives of the present invention are: 1). To greatly minimize shaving toxicity through the use of unusually large lubricating molecules which can not penetrate skin; 2). To more highly lubricate skin and further protect skin from damage, both during and after shaving; 3). To simultaneously minimize hair shaft lubrication while maximizing hair shaft hydration; 4). To cut hair ends more perpendicularly, which produces considerably closer shaves; and 5). To significantly extend the time periods between shaving.

Briefly, the present invention is directed to a new and unique lubrication for use in shaving, wherein a di-lubricant is applied to the skin in the usual way, but only the skin is lubricated; the hair itself is not be lubricated. The present invention represents a quantum departure from the old universal lubrication concept. Very large water-molecule lubricants, as formulated herein, are used, and these not only provide the desired lubrication of the skin, but not the hair, they also exhibit unusually low toxicity, which make them useful for many other general medical lubricant applications.

Di-lubrication provides a high degree of slippage between the skin and a razor, to permit the application of pressure to cut hair below the skin level without damage to the skin. In addition, since it does not lubricate the hair, it ensures zero micro-slippage, and therefore an instant grip of the razor upon initial microscopic contact of the razor edge with each hair shaft, and this produces perpendicularly-cut hair rather than tapered cut hair shafts. The result is considerably closer and significantly longer lasting shaves, up to almost twice that of prior art of shaving lubricants, while at the same time maximizing skin hydroplaning for minimal skin damage. Since skin is a highly porous organ and is a direct path for toxins to enter the body, the preferred embodiment of the present invention also achieves extremely low toxicity through the use of extra large lubricant molecular structures, composed of essentially water, which cannot penetrate the microprobes of skin.

In one preferred embodiment of an ideal di-lubricant formulation, unusually small concentrations of fully hydrated, extra-long-chain, purified flocculant polyacrylamide molecules are suspended like soft microscopic ball bearings in water. Under these conditions of ultra low concentrations, polyacrylamide transforms from a known excellent lubricant into a high performance differential lubricant with very unexpected new hair shaving properties. The preferred di-lubricant essentially consists of highly nontoxic gigantic polyacrylamide water-spheroids of 99.9+% water; which are designed to act like soft ball bearings between razor and skin, but which molecularly self-destruct when subjected to the considerably higher mechanical pressures (force per unit area) encountered between razors and relatively hard hair shafts, thus producing near zero lubrication on each hair shaft. When these two distinctly opposite (lubricant/non-lubricant) physical properties are combined with the low viscosity of water, razors freely slide and hydroplane over skin, but exhibit no microscopic slippage on hair. High shaving forces can be applied without razor burns, skin cutting or nicking—allowing even closer shaves than prior art lubricants. The lack of an effective lubricant on the hair results in near zeromicroscopic slippage of the razor on the hair shafts and causes the hair to be cut perpendicularly, and thus considerably shorter, than was possible with the sharp tapered hair shaft cuts of the prior art. Less damaged skin, shorter hair cutting, and greatly reduced toxicity are the unexpected results of the present invention's unique di-lubrication formulations. Finally, it is important to reemphasize that di-lubrication represents a distinct and radical departure from all prior art general purpose lubricated shaving, and that many other di-lubricant formulations are possible—none of which materially depart from the scope and intent of the present invention.

BRIEF DESCRIPTION OF THE DRAWINGS

The foregoing, and additional objects, features and advantages of the invention will become apparent to those of skill in the art upon consideration of the following detailed description of preferred embodiments thereof, taken with the following drawings, in which.

DESCRIPTION OF PREFERRED EMBODIMENTS

Figure 1:
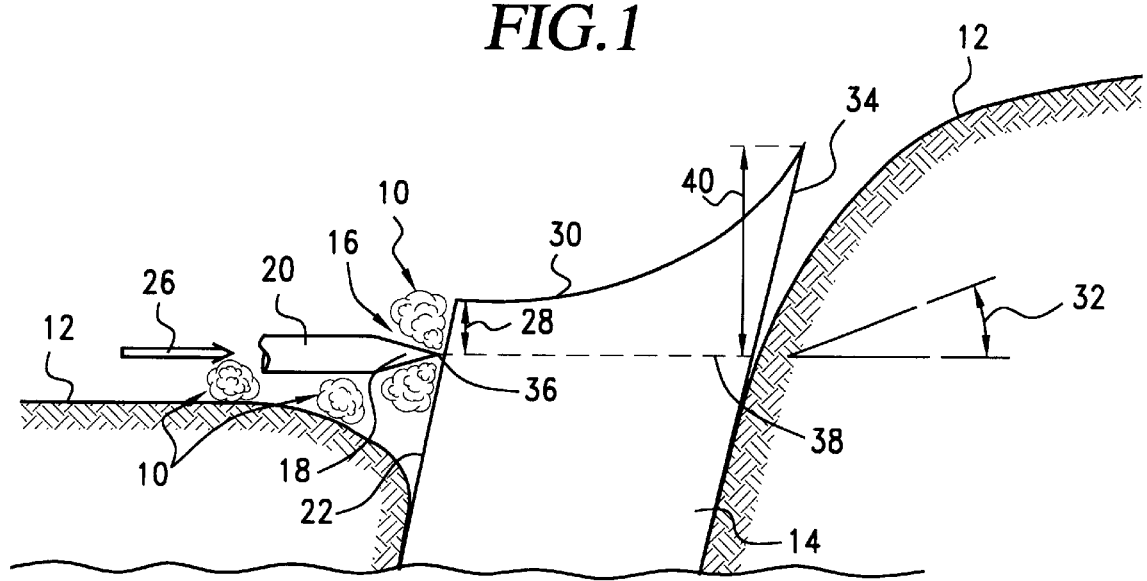
FIG. 1 is a diagrammatic illustration of the interaction between a hair shaft and a razor blade as the blade is drawn across the skin during shaving.

Di-lubrication, as applied to the present invention, means any lubricant of any composition, which by way of any physical or chemical means, achieves distinctly different lubricating properties of skin versus hair. More specifically, in hair shaving applications, as diagrammatically illustrated in FIG. 1, a di-lubricant 10 according to the invention causes the skin 12 to be highly lubricated and the hair 14 to be minimally lubricated.

One class of di-lubricants is represented by molecules having ultra weak chemical bonds which are designed to disintegrate upon the application of high mechanical shaving forces. When such weak molecular structures are used as shaving lubricants, the weakly bonded structure is mechanically broken, as illustrated at 16 when a molecule 10 is trapped between the edge 18 of a razor 20 and the surface 22 of the hair shaft 14. When this occurs, the lubricating properties are destroyed, as at 16, so the edge 18 contacts the surface 22 and there is little or no slippage between the razor's edge and the hair shaft. And yet, the bulk lubricating properties of the shaving lubricant molecules 10 are not so weak as to mechanically disintegrate when trapped between the razor and the relatively soft skin, as at 24, so that the skin 12 remains lubricated. This general approach to di-lubrication takes advantage of the difference in relative hardness of soft skin and hard hair shafts. Skin is considerably softer and more pliable than hard hair shafts, and as such, skin more readily distributes the applied shaving forces (pressure) over a much greater surface area, thus producing a comparatively mild mechanical pressure (force per unit area) between the razor 20 and the skin. By contrast, when a hard straight razor edge 18 contacts a relatively hard cylindrical hair shaft 14 with essentially a point contact (near zero surface area), the localized pressure (force per unit area) is several orders of magnitude greater than the pressure between the razor and the pliable skin. It is this differential pressure which can be taken advantage of to create the differential lubrication (or "di-lubricating") properties of the present invention.

Long chain soap and surfactant agglomerated polymers are examples of weakly bound large molecular structures which will differentially self destruct between skin and hair. Such molecular structures are easily formed by allowing dilute solutions of soapy water to stand undisturbed for many days. A very slippery and slimy solution forms so that when a small sample is extracted from the bulk solution, long stringers follow the extracted sample. When gently applied to the skin, it exhibits very high skin lubricating properties. However, the weak hydrogen bonds and delicate micelle-like complex molecular structures of this group of di-lubricants are so delicate that mere vigorous commercial shipping can degrade their long chain di-lubricating properties from their optimum performance.

A preferred example of di-lubrication is achieved with exceedingly dilute, water soluble, very high molecular weight polyacrylamide, of about 14 million molecular weight. Although water based polyacrylamide is well known to be very slippery, hair shaving di-lubrication properties are completely unknown prior to the present invention. Although U.S. Pat. No. 3,072,536 disclose the highly lubricating properties of 0.5% to 4% polyacrylamide (500,000 MW) concentrations in a water solvent, such high concentrations and low molecular weights do not provide the di-lubrication effects of the present invention. It has now been found that when about 20 times higher molecular weight polyacrylamide, plus its concentrations, are reduced to as low as 0.02% (200 times less than that proposed in U.S. Pat. No. 3,072,536), di-lubricity occurs.

Microscopic inspections of di-lubricated hair, as illustrated in FIG. 1, shows that the cut hairs are surprisingly different and much more perpendicularly cut, than those cut using prior shaving lubricants. As illustrated, when hair is cut using conventional lubricants, the surface 22 of the hair is slippery, so that as the razor is moved to cut the hair (in the direction of arrow 26) it slides up the hair shaft a small distance 28 before starting to cut. The lubricant on the blade causes additional slippage, with the result that the top 30 of the hair shaft is cut at an angle 32, leaving a tapered hair that may extend above the surface of the skin, as at 34. In fact, the final shaved length of lubricated hair is proportional to the thickness of the hair shaft being shaved. A second pass of the razor is often required in order to cut the tapered remains of the hair shaft. On the other hand, with the di-lubricant of the present invention, the edge 28 of the razor mechanically breaks through the lubricant 10 and reaches the surface 20 of the hair at point 36. Since the hair is not lubricated at this point, the edge 18 tends to cut into the hair at that point, and since the blade is not lubricated it tends to cut directly through the hair at a lower cutting angle, generally along the dotted line 38, which is generally perpendicular to the vertical axis of the hair shaft 14. Hair shafts that are more perpendicularly cut are significantly shorter, as illustrated at 40, and this is a result of the di-lubricant cutting action.

The result of di-lubrication, therefore, is increased razor pressure as a result of increased lubricity and decreased viscosity, which in turn, produces a shorter hair. Decreased hair lubrication also reduces razor slippage and shortened hair (7).

Di-lubrication occurs when about 0.02% to 0.5% (by weight) concentrations of 14 million molecular weight polyacrylamide (20 times the MW) is gently dispersed in water. That is, skin is highly lubricated—the first priority of shaving and hair shafts remain remarkably unlubricated and behave as if they were immersed only in pure water.

Hair hydration is also desirable and highly recommended by razor blade manufacturers to reduce dulling of razor blades. Therefore, the above 99+% water based formulation is also ideal for maximum hydration. The ultra low viscosity of this formulation approaches that of water itself, and as a result, produces very low viscous drag on the skin, allowing even higher applied vertical razor forces for closer shaves. (Very high viscous drag causes skin to stretch toward tearing, causing potentially deep razor cuts). The 20×higher molecular weight polyacrylamide produces swollen hydrogen bonded water spheroids 10, illustrated diagrammatically in FIG. 2, which may be in excess of 200 nanometers in diameter. These act like soft water ball bearings on soft skin. The low concentration of the polyacrylamide in the water results in a low number of these large water spheroids per unit area (low density of spheroids), but still allows razors to slide and essentially hydroplane across soft skin. However, the density of the spheroids (that is, the number of spheroids per unit area) is too low to completely coat or lubricate hair shafts from the razor's edge, and the crushing point-contact pressures of the razor edge on the hair shaft are great enough to exceed the delicate mechanical limits of swollen polyacrylamide. Hence, hydroplaning and lubricating activity on hair shafts is greatly reduced or eliminated. The phrase "delicate mechanical limits" is a very appropriate term to apply to swollen polyacrylamide. In fact, when a batch of fully hydrated 14 million molecular weight polyacrylamide is subjected to a simple high speed blender for just a few seconds, it is destroyed. Lubricating properties greatly diminish and viscosity decreases. Lower molecular weight lubricants (such as 500,000 molecular weight in prior art shaving publications) are much more resistant to such mechanical destruction. Mechanical molecular destruction is inversely proportional to molecular weight. Hence, the larger the hydrated molecule (in the present invention: 14 million vs. 500,000 in the prior art), the more easily its lubricating properties are mechanically destroyed. A balance between destruction and non-destruction (and of course, lubricity and non lubricity) is required in order to lubricate soft skin and not lubricate hard hair. The above formulation is but one example of that balance which creates the desired di-lubricity properties.

Much polyacrylamide manufacturing research has been completed since it was first invented. Various methods to completely polymerize acrylamide monomers, as well as methods to scavenge small remainder quantities of toxic acrylamide monomers, have been developed. However, at high doses, acrylamide monomers were once considered carcinogens and repeated applications of the polyacrylamide in prior art shaving formulations could have unknowingly subjected people to very large concentrations of carcinogens. The current body of knowledge on monomer reduction is so improved that polyacrylamide is now used in municipal water purification processing. Even the most demanding States, such as California, allow purified polyacrylamide as the particulate scavenger of dirty water. The present invention furthers that cause by not only employing highly purified polyacrylamide, having almost no acrylamide monomers, but by also reducing the concentrations of purified polyacrylamide by roughly 10 or more times less than the prior art. Therefore, all concerns of toxicity are completely eliminated from the present invention. Moreover, if about 1 to 2 PPM of Sodium Meta Bisulfite is blended in during the production of the present invention's formulation, it will further scavenge even the most minute trace acrylamide monomers. Small chain polyacrylamide molecules are largely eliminated from the present invention's formulation by using 14 million molecular weight molecules, such as that produced by Cytec Industries (product number N-300, non ionic polyacrylamide granules). The preponderance of these extra large molecules grow about 100 fold in physical size (volume) when fully hydrated, from about 33 nanometers in diameter (dry) to larger than about 200 nanometers in diameter (when fully hydrated).

Figure 2:
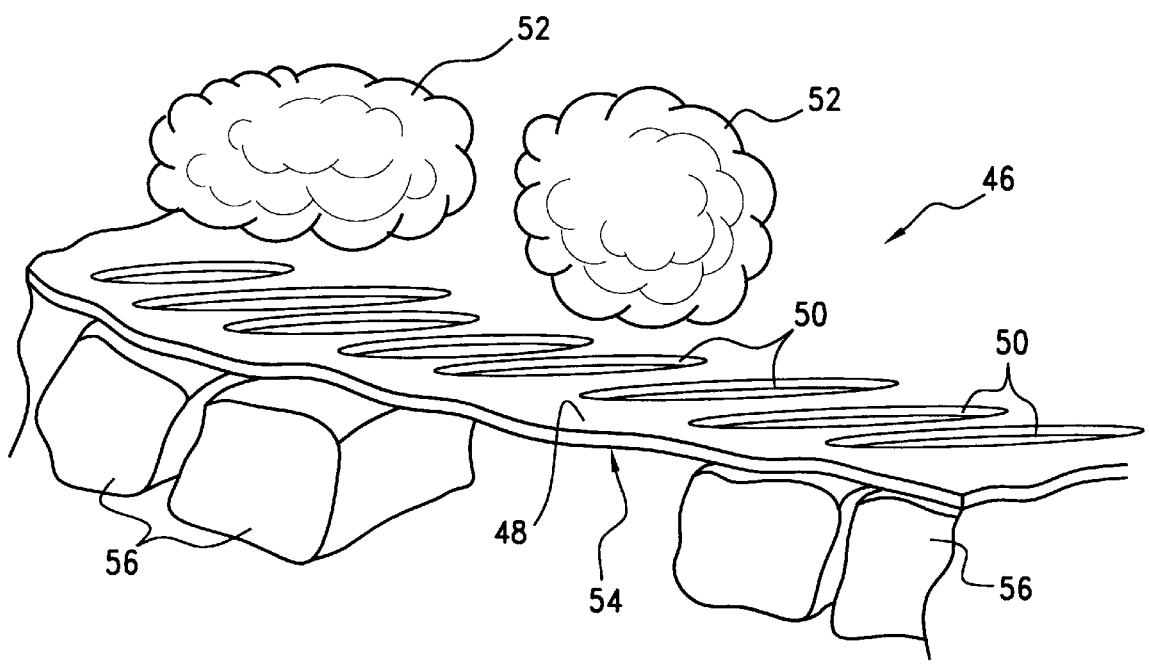
FIG. 2 is a diagrammatic illustration of a di-lubricant, in accordance with the invention, on the surface of the skin.

FIG. 2 depicts the nontoxic effects of employing unusually large and hydrogen bonded polyacrylamide on skin, generally indicated at 46. The horny layer (stratum corneum) 48 is the greatest protection barrier of the skin. A dry horny layer has cleavage spaces 50 on the order of 1–10 nanometers in width, through which most toxic molecules, which are much smaller than 10 nanometers, can freely enter the body. Extremely high molecular weight polyacrylamide molecules 52, such as 14 million MW (33 NM dry), are about 200 nanometers in diameter when swollen with water to about 100 times their own weight. Such extremely large structures 52 cannot penetrate the skin openings 50 in the outer protective horny layer 48 (above line 54) nor the passages between live skin cells depicted at 56 below line 54. Since the di-lubricant of the present invention is composed of well over 99% hydrogen bonded water, and is also physically much larger than the openings in skin, they can not enter the body. Even if such a structure could be forced under the horny layer, it could not penetrate the cellular layers. Furthermore, purified polyacrylamide (without monomers) has no known adverse reactions in the body. Toxicity simply is not a concern.

To make this point clearer, dry 14 million MW polyacrylamide molecules of 33 NM diameter will not pass through dry skin with <10 NM pores. Hydrated 14 million MW polyacrylamide molecules (>200 NM) will not pass through hydrated skin with 20–100 NM pores. In this example, skin behaves like a molecular screen to such physically large lubricating water/polyacrylamide spheroids both during shaving, when swollen, and after shaving, when dried. Hence, the present invention is extremely non toxic from every known viewpoint. When formulating the above preferred embodiment of the present invention, the pH of the solution can range from neutral to slightly acidic (5.5 pH), depending on the degree of water deneralization. Therefore, for even the most sensitive skin, the above formulation should be neutralized with a mild caustic such as sodium bicarbonate (baking soda), or the like, to achieve a pH of about 7.

From a practical and commercial viewpoint, the present invention has many other attractions. It can be shipped with vigorous agitation without damage to the moderately delicate molecules. It can be frozen and thawed with no damage. It can be heated to 180 degrees F for up to 30 days with insignificant damage. It can be exposed to bacteria for up to two years with no cloudiness or odors forming, thus indicating that it acts as a bacterio-stat where microorganisms become immobilized and effectively sterilized. Prior to the present invention, this bacterio-static property was not previously known. Hence, with this new discovery, no additional chemical preservatives are required in the preferred embodiment. The preferred embodiment of this invention exhibits no taste or smell, can be ingested in extremely large quantities (gallons) with no known side effects, does not stain clothing because it is transparent and colorless. Unlike opaque shaving foams, its transparency allows shavers to see and avoid skin blemishes.

In a broader sense, di-lubrication is now understood well enough to be simulated under a wide variety of conditions. There now exists a wide variety of water soluble long chain polymers and copolymers which can, under the conditions laid out in the present invention, produce di-lubricity. If toxicity were not of concern (but should always be a priority), then smaller molecular weight lubricants, when highly diluted to a very narrow concentration range, also mimic di-lubrication. Perhaps not ideal di-lubricants for shaving, but nonetheless, still di-lubricants, can be created such that the dilution factor alone barely exhibits lubricating properties on skin but not on hair. In other words, slightly more dilution from its optimum dilution removes almost all the skin lubricating properties as well as hair lubrication.

Initially, even to those skilled in the art of lubricated shaving, it defies logic that lubricity and nonlubricity can simultaneously coexist, but the present invention clearly demonstrates methods of achieving these completely new and highly desirable objectives. The prior art has sought only general lubricity of both skin and hair, and has not recognized the possibility or the desirability of lubricating just skin and not hair for shaving. Since lubricated hair can't be cut as short, prior art approaches require multiple razor passes to achieve shorter hair shaves. Moreover, when a hair shaft is highly tapered, effectively thinner and easier to flex, even less lubrication is required—all the more reason to use a di-lubricant in order to prevent razor slippage on thinner hair.

Shaving lubricant toxicity is finally overcome by the present invention, not just by employing low toxicity starting materials, but by preventing them from migrating into the body. When skin research discovered how skin works as a protective barrier, the design of large molecule non toxic shaving di-lubricants became desirable. The present invention has combined excellent lubrication with nonlubrication, plus molecular skin barrier toxin protection, all into one product. Many other non-shaving related applications are also possible for such slippery, di-lubricating, and extremely nontoxic properties. For example, veterinary applications abound. Large animals, such as cattle, are frequently manually examined gynecologically, and low cost, nontoxic lubricants are necessary. Birthing lubricants are also another application. Conjugal lubrication is still another application. Medical probe lubrication is one more excellent application. The preferred embodiment of the present invention is, for all practical purposes, a 99.5% to 99.98% water large-molecule lubricant, and as such, cannot be much more non toxic compared to every prior art medical lubricant.

The di-lubricant properties of the present invention represents new milestones in cosmetic shaving lubricants, designed to achieve closer and longer lasting shaves with the least skin damage, plus near zero toxicity. Likewise, the non-intrusive medical applications of the present invention represent another milestone in lubrication. Many variations of the preferred embodiment of this invention are possible without departing from the broad scope and intents of the present invention.

What is claimed is:

1. A shaving lubricant having differential lubricating qualities for skin and hair, consisting essentially of a high molecular weight, low-concentration solution of polyacrylamide suspended in water, the concentration of polyacrylamide being about 0.02 and 0.5 percent by weight for a polyacrylamide material having a molecular weight of about 14 million, whereby the lubricant causes skin to be highly lubricated and hair to be minimally lubricated.

* * * * *